United States Patent
Diolaiti et al.

(10) Patent No.: US 12,364,556 B2
(45) Date of Patent: Jul. 22, 2025

(54) SYSTEMS AND METHODS FOR DEVICE VERIFICATION AND SENSOR CALIBRATION

(71) Applicant: Intuitive Surgical Operations, Inc., Sunnyvale, CA (US)

(72) Inventors: Nicola Diolaiti, San Francisco, CA (US); Wanxi Liu, Foster City, CA (US); Samuel B. Schorr, East Palo Alto, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 1155 days.

(21) Appl. No.: 17/279,730

(22) PCT Filed: Oct. 1, 2019

(86) PCT No.: PCT/US2019/053928
§ 371 (c)(1),
(2) Date: Mar. 25, 2021

(87) PCT Pub. No.: WO2020/072398
PCT Pub. Date: Apr. 9, 2020

(65) Prior Publication Data
US 2021/0393349 A1 Dec. 23, 2021

Related U.S. Application Data

(60) Provisional application No. 62/741,242, filed on Oct. 4, 2018.

(51) Int. Cl.
*A61B 34/20* (2016.01)
*A61B 34/37* (2016.01)
*A61B 90/00* (2016.01)

(52) U.S. Cl.
CPC ........... *A61B 34/37* (2016.02); *A61B 34/20* (2016.02); *A61B 90/37* (2016.02);
(Continued)

(58) Field of Classification Search
CPC ......... A61B 34/37; A61B 34/20; A61B 90/37; A61B 2034/2051; A61B 2034/2055;
(Continued)

(56) References Cited

U.S. PATENT DOCUMENTS

| 6,380,732 B1 | 4/2002 | Gilboa |
| 6,389,187 B1 | 5/2002 | Greenaway et al. |

(Continued)

FOREIGN PATENT DOCUMENTS

| CN | 105979848 A | 9/2016 |
| EP | 3111819 A1 | 1/2017 |

(Continued)

OTHER PUBLICATIONS

S. Hasanzadeh, F. Janabi-Sharifi, P. Keenan, Backlash characterization and position control of a robotic catheter manipulator using experimentally-based kinematic model, Mechatronics, vol. 44, 2017, pp. 94-106, ISSN 0957-4158, https://doi.org/10.1016/j.mechatronics.2017.05.002 (Year: 2017).*

(Continued)

*Primary Examiner* — Jaime Figueroa
(74) *Attorney, Agent, or Firm* — Haynes & Boone, LLP (57) ABSTRACT

Systems and methods for verification and calibration of robotic instruments are provided. A robotic system may include an instrument carriage to receive an elongate device, and the instrument carriage may comprise a set of drive sensors. The system may also include a tracking system configured to receive an indication that the elongate device is installed on the instrument carriage, operate a set of actuators to articulate a distal portion of the elongate device, (Continued)

and generate a set of drive sensor data from the set of drive sensors. The tracking system may also be configured to generate a set of articulation sensor data from a shape sensor of the elongate device, compare the set of drive sensor data to the set of articulation sensor data to generate a test profile, and determine whether the test profile corresponds to a reference profile. Corrective action may be determined.

20 Claims, 6 Drawing Sheets

(52) U.S. Cl.
CPC ............. *A61B 2034/2051* (2016.02); *A61B 2034/2055* (2016.02); *A61B 2034/2059* (2016.02); *A61B 2034/2061* (2016.02); *A61B 2090/3735* (2016.02); *A61B 2090/374* (2016.02); *A61B 2090/3762* (2016.02); *A61B 2090/378* (2016.02); *A61B 2560/0223* (2013.01)

(58) Field of Classification Search
CPC .... A61B 2034/2059; A61B 2034/2061; A61B 2090/3735; A61B 2090/374; A61B 2090/3762; A61B 2090/378; A61B 2560/0223

See application file for complete search history.

(56) References Cited

U.S. PATENT DOCUMENTS

| | | | |
|---|---|---|---|
| 7,048,745 B2 | 5/2006 | Tierney et al. | |
| 7,316,681 B2 | 1/2008 | Madhani et al. | |
| 9,259,274 B2 | 2/2016 | Prisco | |
| 11,129,962 B2* | 9/2021 | Govari | A61B 34/20 |
| 11,759,262 B2 | 9/2023 | Barbagli et al. | |
| 2006/0013523 A1 | 1/2006 | Childers et al. | |
| 2008/0212082 A1 | 9/2008 | Froggatt et al. | |
| 2013/0345718 A1* | 12/2013 | Crawford | A61B 34/76 606/130 |
| 2016/0374541 A1 | 12/2016 | Agrawal et al. | |
| 2018/0256262 A1 | 9/2018 | Duindam et al. | |
| 2018/0353252 A1* | 12/2018 | Chassot | A61B 34/71 |
| 2019/0212761 A1* | 7/2019 | Swanson | A61B 5/0075 |

FOREIGN PATENT DOCUMENTS

| | | |
|---|---|---|
| EP | 3111819 B1 | 12/2018 |
| WO | WO-2016164311 A1 | 10/2016 |
| WO | WO-2016191298 A1 | 12/2016 |
| WO | WO-2017044874 A1 | 3/2017 |
| WO | WO-2018005861 A1 | 1/2018 |

OTHER PUBLICATIONS

International Preliminary Report on Patentability for Application No. PCT/US2019/053928, mailed on Apr. 15, 2021, 14 pages.

International Search Report and Written Opinion for Application No. PCT/US2019/053928, mailed on Jan. 27, 2020, 20 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Office Action for Chinese Application No. CN201980065604.5, mailed Aug. 10, 2024, 21 pages.

Office Action for Chinese Application No. CN201980065604.5, mailed Nov. 30, 2023, 21 pages.

* cited by examiner

SYSTEMS AND METHODS FOR DEVICE VERIFICATION AND SENSOR CALIBRATION

CROSS-REFERENCE TO RELATED APPLICATIONS

This application is the U.S. national phase of International Application No. PCT/US2019/053928, filed Oct. 1, 2019, which designates the U.S. and claims priority to and the benefit of U.S. Provisional Application 62/741,242 filed Oct. 4, 2018, both of which are incorporated by reference herein in their entirety.

FIELD

Examples described herein relate to systems and methods for a procedure, such as systems and methods for verifying the operation of a system and for calibrating sensors of the system.

BACKGROUND

Instruments can be used to manipulate and perform tasks in a work space. Such instruments may be configured to be supported and operated partially or entirely by manipulator assemblies. Such instruments and manipulator assemblies can be used to perform non-medical procedures or medical procedures. For example, medical tools or medical manipulators can be used to perform minimally invasive medical procedures. As another example, industrial tools or industrial manipulators can be used in manufacture or testing. As yet other examples, tools or manipulators can be used in procedures for entertainment, exploration, and various other purposes.

Minimally invasive medical techniques may generally be intended to reduce the amount of tissue that is damaged during invasive medical procedures, thereby reducing patient recovery time, discomfort, and harmful side effects. Such minimally invasive techniques may be performed through natural orifices in a patient anatomy or through one or more incisions. Through these natural orifices or incisions, clinicians may insert medical tools to reach a target tissue location. Minimally invasive medical tools include instruments such as therapeutic instruments, diagnostic instruments, and surgical instruments. Minimally invasive medical tools may also include imaging instruments such as endoscopic instruments that provide a user with a field of view within the patient anatomy.

Some medical and non-medical instruments (including manipulation instruments, imaging instruments or other sensing instruments, etc.) may be teleoperated or otherwise computer-assisted. Prior to performing a procedure with a system that includes an instrument, safe and reliable mechanisms are desired to verify that the system and the instrument are operating properly and to calibrate sensors of the system.

SUMMARY

The following presents a simplified summary of various examples described herein and is not intended to identify key or critical elements or to delineate the scope of the claims.

A robotic system may include an instrument carriage configured to receive an elongate device. The instrument carriage may comprise a set of actuators configured to drive the elongate device along at least one degree of freedom and a set of drive sensors configured to monitor the set of actuators. The robotic system may also include a tracking system coupled to the instrument carriage and configured to receive an indication that the elongate device is installed on the instrument carriage and operate the set of actuators to articulate a distal portion of the elongate device in at least one degree of freedom. The tracking system may also generate a set of drive sensor data from the set of drive sensors during the articulation, generate a set of articulation sensor data from a shape sensor of the elongate device during the articulation, and compare the set of drive sensor data to the set of articulation sensor data to generate a test profile. The tracking system may also determine whether the test profile corresponds to a reference profile and determine whether a corrective action is needed for the elongate device based on whether the test profile corresponds to the reference profile.

In another example, an apparatus comprises one or more processors and non-transitory computer memory storing machine-executable instructions that, when executed by the one or more processors, cause the apparatus to receive an indication that a flexible elongate device is coupled to a drive unit and command articulation of a distal portion of the flexible elongate device in at least one degree of freedom. The instructions may also cause the apparatus to receive a set of drive sensor data during the articulation, receive a set of articulation sensor data during the articulation, and compare the set of the drive sensor data to the set of the articulation sensor data to generate a test profile. The instructions may also cause the apparatus to determine whether the test profile meets one or more thresholds in a reference profile and determine whether to perform a corrective action based on whether the test profile meets the one or more thresholds.

In another example, method of performing a calibration testing sequence for a robotic system may include receiving an indication that a flexible elongate device is coupled to a drive system of the robotic system, the drive system including one or more drive system sensors and commanding articulation of the flexible elongate device in at least one degree of freedom. The method may also include generating drive sensor data from the one or more drive system sensors during the commanded articulation, generating articulation sensor data from an articulation sensor of the flexible elongate device during the commanded articulation, and comparing the drive sensor data to the articulation sensor data to generate a test profile. The method may also include determining whether the test profile corresponds to a reference profile and determining whether a corrective action is needed for the flexible elongate device based on the determining whether the test profile corresponds to the reference profile.

It is to be understood that both the foregoing general description and the following detailed description are illustrative and explanatory in nature and are intended to provide an understanding of the present disclosure without limiting the scope of the present disclosure. In that regard, additional aspects, features, and advantages of the present disclosure will be apparent to one skilled in the art from the following detailed description.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

The technology described herein provides for testing and calibrating a robotic device or system, such as during system startup or power up. The disclosed technology for testing and calibration can be implemented on any robotic device or system, including those that implement a user-installable, or user-replaceable instrument with embedded sensors, actuators, or a combination of both sensors and actuators. Examples of applicable robotic devices or systems include medical devices, teleoperated or otherwise operated, that utilize resposable instruments that undergo cleaning and reprocessing in between uses. As an illustrative and enabling example, various aspects of the disclosed technology are described with respect to an example flexible robotic device or system, such as a robotically controlled catheter described with respect to FIGS. 1, 2A, and 2B. In various embodiments, a robotically controlled catheter can include sensors to identify position and shape of the catheter, such as a fiber optic sensor for shape sensing and localization. The sensors, such as a fiber sensor, may provide real time localization data used for navigation and/or for closed loop control during articulation of the catheter. The disclosed technology for testing and calibration as described with respect to FIGS. 4, 5A, 5B, and 6 can be implemented to provide a number of advantages including ensuring proper alignment of the sensor, such as the fiber sensor, and stable control loops.

Figure 1:
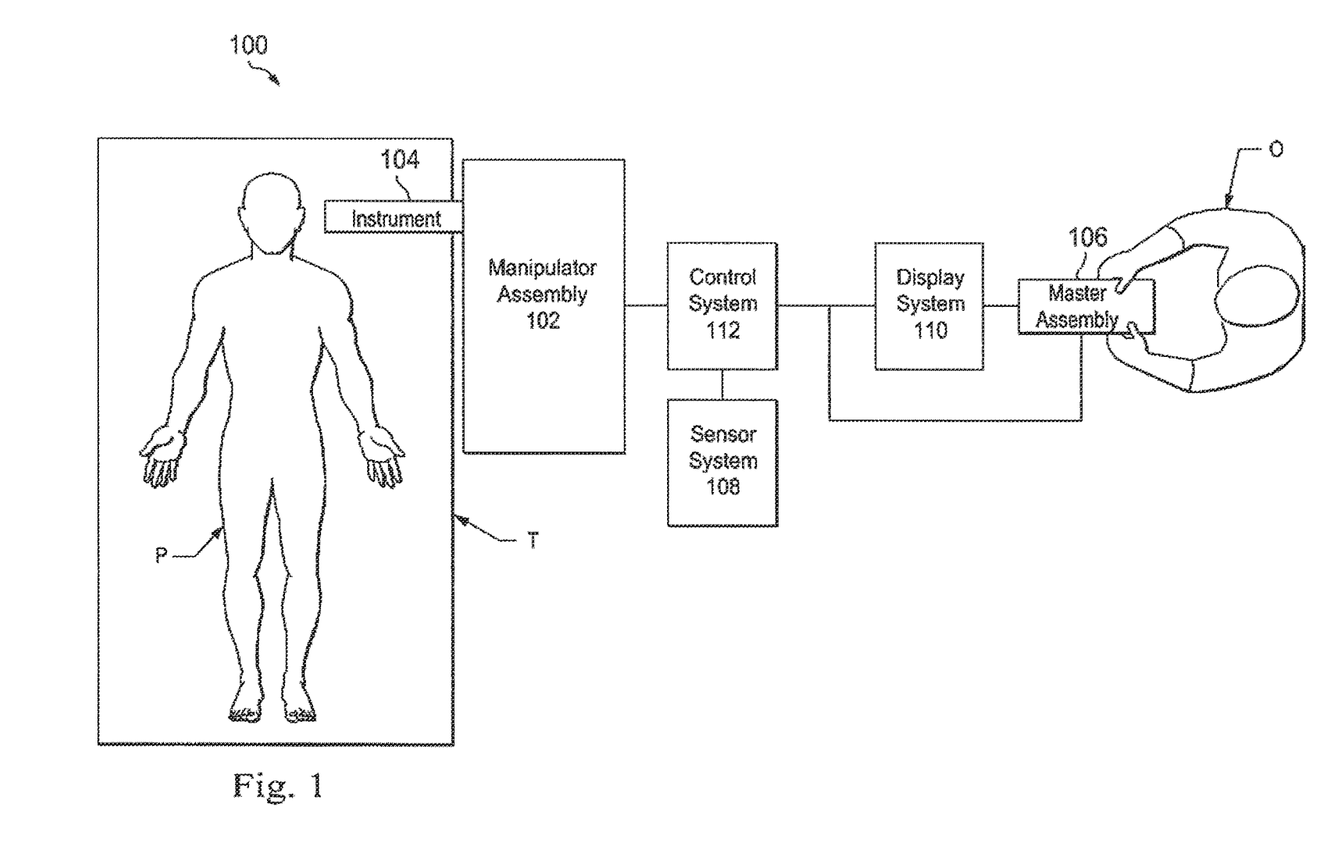
FIG. 1 is a simplified diagram of a medical system according to some embodiments.

FIG. 1 is a simplified diagram of a robotic medical system 100 according to some embodiments. In some embodiments, medical system 100 may be suitable for use in, for example, surgical, diagnostic, therapeutic, or biopsy procedures. While some embodiments are provided herein with respect to such procedures, any reference to medical or surgical instruments and medical or surgical methods is non-limiting. The systems, instruments, and methods described herein may be used in robotic systems for animals, human cadavers, animal cadavers, portions of human or animal anatomy, non-surgical diagnosis, as well as for industrial systems and/or other general robotic systems.

As shown in FIG. 1, medical system 100 may include a manipulator assembly 102 for operating a medical instrument 104 in performing various procedures on a patient P. Medical instrument 104 may extend into an internal site within the body of patient P via an opening in the body of patient P. The manipulator assembly 102 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. Manipulator assembly 102 may be mounted to and/or positioned near an operating table T. A master assembly 106 allows an operator O (e.g., a surgeon, a clinician, or a physician as illustrated in FIG. 1) to view the interventional site and to control manipulator assembly 102.

Master assembly 106 may be located at an operator console which is may be located in the same room as operating table T, such as at the side of a surgical table on which patient P is located. However, it should be understood that operator O can be located in a different room or a completely different building from patient P. Master assembly 106 generally includes one or more control devices for controlling manipulator assembly 102. The control devices may include any number of a variety of input devices, such as joysticks, trackballs, scroll wheels, directional pads, buttons, data gloves, trigger-guns, hand-operated controllers, voice recognition devices, body motion or presence sensors, and/or the like.

Manipulator assembly 102 supports medical instrument 104 and may include: kinematic structure of one or more non-servo controlled links (e.g., one or more links that may be manually positioned and locked in place, generally referred to as a set-up structure), one or more servo controlled links (e.g., one or more links that may be controlled in response to commands from the control system), and/or a manipulator. Manipulator assembly 102 may include a plurality of actuators or motors that drive inputs on medical instrument 104 in response to commands from the control system (e.g., a control system 112). The actuators may include drive systems that when coupled to medical instrument 104 may advance medical instrument 104 into a naturally or surgically created anatomic orifice. Other drive systems may move the distal portion of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like.

Medical system 100 may include a sensor system 108 with one or more sub-systems for receiving information about the manipulator assembly 102 and/or the medical instrument 104. Such sub-systems may include a position/location sensor system (e.g., an electromagnetic (EM) sensor system); a shape sensor system for determining the position, orientation, speed, velocity, pose, and/or shape of a distal portion and/or of one or more segments along a flexible body that may make up medical instrument 104; a visualization system for capturing images from the distal portion of medical instrument 104; and/or actuator position sensors such as resolvers, encoders, potentiometers, and the like that describe the rotation and orientation of the motors controlling the instrument 104.

Medical system 100 may include a display system 110 for displaying an image or representation of the surgical site and medical instrument 104. In some examples, display system 110 may present pre-operative or intra-operative images of a surgical site using image modalities such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. In some embodiments, medical instrument 104 may include a visualization system that includes an image capture assembly to record a concurrent or real-time image of a surgical site and to provide the image to the operator O through one or more displays of display system 110.

In some examples, medical system 100 may configure the displayed representations, the medical instrument 104, and the controls of master assembly 106 such that the relative positions of the medical instruments are similar to the relative positions of the eyes and/or hands of operator O. In this manner, operator O can manipulate medical instrument 104 and hand controls as if viewing the workspace in substantially true presence.

In some examples, such as for purposes of image-guided medical procedures, display system 110 may display a virtual navigational image in which the actual location of medical instrument 104 is registered (e.g., dynamically referenced) with the preoperative or concurrent images/model. This may be done to present the operator O with a virtual image of the internal surgical site from a viewpoint of medical instrument 104.

Medical system 100 may also include control system 112. Control system 112 includes at least one memory and at least one computer processor (not shown) for effecting control between manipulator assembly 102, medical instrument 104, master assembly 106, sensor system 108, and/or display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to manipulator assembly 102, another portion of the processing being performed at master assembly 106, and/or the like. The processors of control system 112 may execute instructions corresponding to processes disclosed herein and described in more detail below.

In some examples, control system 112 may receive force and/or torque feedback from medical instrument 104. Responsive to the feedback, control system 112 may transmit signals to master assembly 106. In some examples, control system 112 may transmit signals instructing one or more actuators of manipulator assembly 102 to move medical instrument 104.

Control system 112 may obtain sensor data from sensor system 108 that is used to compute an approximate location of medical instrument 104 with respect to the anatomy of patient P. The system may implement the sensor system 108 to register and display the medical instrument together with preoperatively or intraoperatively recorded medical images. For example, PCT Publication WO 2016/191298 (published Dec. 1, 2016 and titled "Systems and Methods of Registration for Image Guided Surgery"), which is incorporated by reference herein in its entirety, discloses example systems.

Medical system 100 may further include operations and support systems such as illumination systems, articulation (e.g., steering) control systems, irrigation systems, and/or suction systems (not shown). In some embodiments, medical system 100 may include more than one manipulator assembly and/or more than one master assembly. The exact number of manipulator assemblies may depend on the medical procedure and space constraints within the operating room, among other factors. Master assembly 106 may be co-located or they may be positioned in separate locations. Multiple master assemblies may allow more than one operator to control one or more manipulator assemblies in various combinations.

Figure 2A:
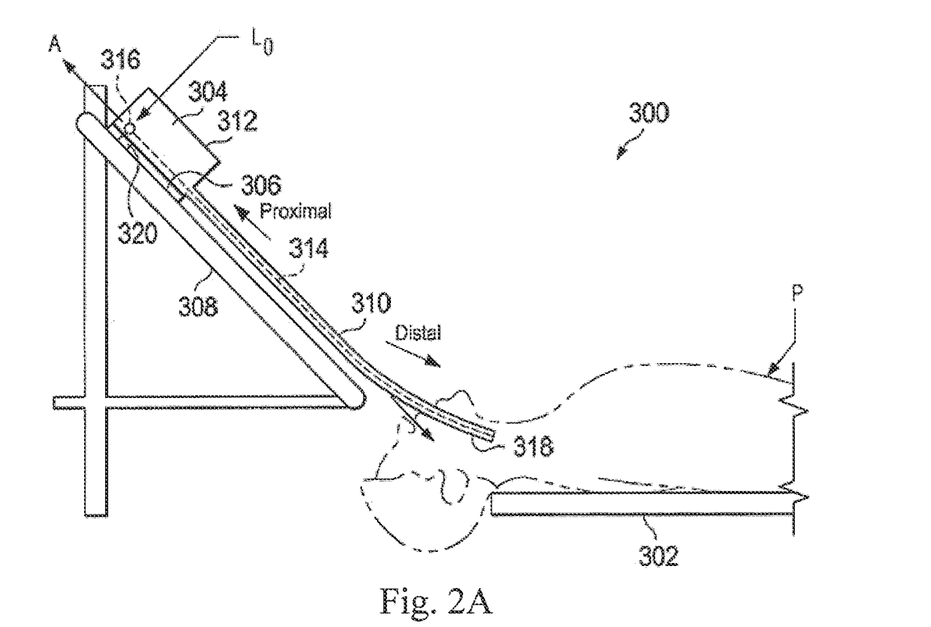
FIGS. 2A and 2B are simplified diagrams of side views of a patient coordinate space including a medical instrument mounted on an insertion assembly according to some embodiments.
Figure 2B:
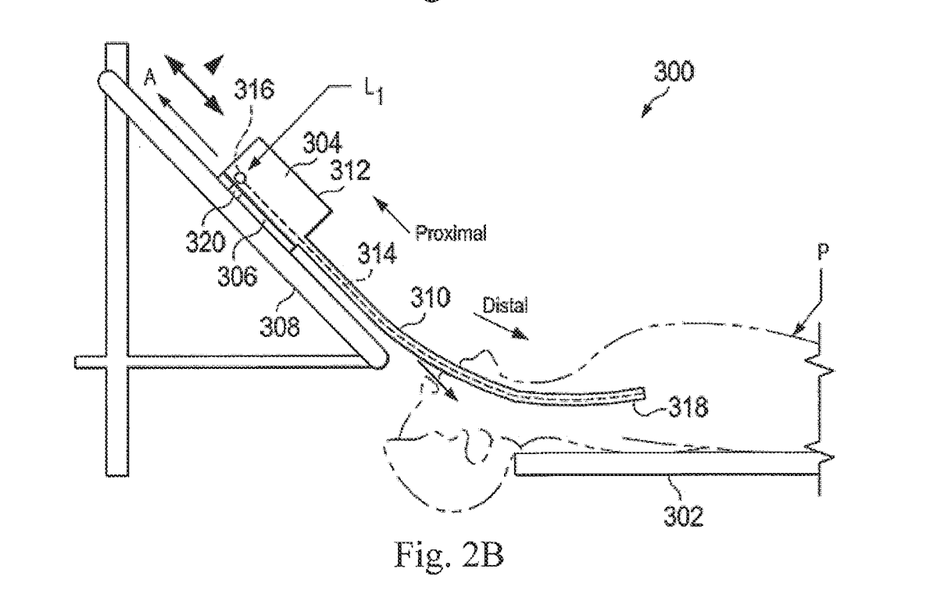

FIGS. 2A and 2B are simplified diagrams of side views of a patient coordinate space including a medical instrument mounted on an insertion assembly according to some embodiments. As shown in FIGS. 2A and 2B, a surgical environment 300 may include a patient P positioned on a table T. Patient P may be stationary within the surgical environment 300 in the sense that gross patient movement is limited by sedation, restraint, and/or other means. Cyclic anatomic motion including respiration and cardiac motion of patient P may continue. Within surgical environment 300, a medical instrument 304 is used to perform a medical procedure which may include, for example, surgery, biopsy, ablation, illumination, irrigation, suction a system registration procedure. The medical instrument 304 may be, for example, the instrument 104. The instrument 304 includes a flexible elongate device 310 (e.g., a catheter) coupled to an instrument body 312. Elongate device 310 includes one or more channels (not shown) sized and shaped to receive a medical tool (not shown).

Elongate device 310 may also include one or more sensors (e.g., components of the sensor system 108). In some examples, an articulation sensor 314, such as a fiber optic shape sensor, may be fixed at a proximal point 316 on instrument body 312. The proximal point 316 of the articulation sensor 314 may be movable with instrument body 312, and the location of the proximal point 316 may be known (e.g., via a tracking sensor or other tracking device). Articulation sensor 314 may measure a shape from the proximal point 316 to another point, such as distal portion 318 of the elongate device 310. Articulation sensor 314 may be aligned with the flexible elongate device 310 (e.g., provided within an interior channel (not shown) or mounted externally). In some examples, the optical fiber may have a diameter of approximately 200 μm. In other examples, the diameter may be larger or smaller. The articulation sensor 314 may be used to determine the shape of flexible elongate device 310. Optical fibers including Fiber Bragg Gratings (FBGs) may be used to provide strain measurements in structures in one or more dimensions. Various systems and methods for monitoring the shape and relative position of an optical fiber in three dimensions are described in U.S. patent application Ser. No. 11/180,389 (filed Jul. 13, 2005 and titled "Fiber optic position and shape sensing device and method relating thereto"); U.S. patent application Ser. No. 12/047,056 (filed on Jul. 16, 2004 and titled "Fiber-optic shape and relative position sensing"); and U.S. Pat. No. 6,389,187 (filed on Jun. 17, 1998 and titled "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. Various systems for using fiber optic sensors to register and display a surgical instrument with surgical images are provided in PCT Publication WO 2016/191298 (published Dec. 1, 2016 and titled "Systems and Methods of Registration for Image Guided Surgery"), which is incorporated by reference herein in its entirety.

In some examples, position sensors such as electromagnetic (EM) sensors, may be incorporated into the medical instrument 304. A series of position sensors may be positioned along the flexible elongate device 310 and used for shape sensing. In some examples, position sensors may be configured and positioned to measure six degrees of freedom, e.g., three position coordinates X, Y, Z and three orientation angles indicating pitch, yaw, and roll of a base point. In some examples, position sensors may be configured and positioned to measure five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999 and titled "Six-Degree of Freedom Tracking System Having a Passive Transponder on the Object Being Tracked"), which is incorporated by reference herein in its entirety.

Elongate device 310 may house cables, linkages, or other steering controls (not shown) that extend between instrument body 312 and distal portion 318 to controllably bend distal portion 318. In some examples, at least four cables are used to provide independent up-down steering to control a pitch of distal portion 318 and left-right steering to control a yaw of distal portion 318. Steerable elongate devices are described in detail in U.S. patent application Ser. No. 13/274,208 (filed Oct. 14, 2011) (disclosing "Catheter with Removable Vision Probe"), which is incorporated by reference herein in its entirety. The instrument body 312 may include drive inputs that removably couple to and receive power from drive elements, such as actuators, of the assembly.

Instrument body 312 may be coupled to instrument carriage 306. Instrument carriage 306 may be mounted to an insertion stage 308 fixed within the surgical environment 300. Alternatively, insertion stage 308 may be movable but have a known location (e.g., via a tracking sensor or other tracking device) within surgical environment 300. Instrument carriage 306 may be a component of a manipulator assembly (e.g., manipulator assembly 102) that couples to medical instrument 304 to control insertion motion (e.g., motion along the A axis) and/or motion of the distal portion 318 of the elongate device 310 in multiple directions such as yaw, pitch, and/or roll. Instrument carriage 306 or insertion stage 308 may include actuators, such as servomotors, (not shown) that control motion of instrument carriage 306 along insertion stage 308.

A sensor device 320, which may be a component of the sensor system 108 may provide information about the position of instrument body 312 as it moves on insertion stage 308 along an insertion axis A. Sensor device 320 may include one or more resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

FIG. 2A shows the instrument body 312 and the instrument carriage 306 in a retracted position along insertion stage 308. In this retracted position, the proximal point 316 is at a position $L_0$ on axis A. In FIG. 2B, instrument body 312 and instrument carriage 306 have advanced along the linear track of insertion stage 308, and the distal portion 318 of elongate device 310 has advanced into patient P. In this advanced position, the proximal point 316 is at a position $L_1$ on the axis A. In some examples, encoder and/or other position data from one or more actuators controlling movement of instrument carriage 306 along insertion stage 308 and/or one or more position sensors associated with instrument carriage 306 and/or insertion stage 308 may be used to determine the position of proximal point 316 relative to position $L_0$. In some examples, this position may further be used as an indicator of the distance or insertion depth to which distal portion 318 of elongate device 310 is inserted into the passageway(s) of the anatomy of patient P.

Figure 3:
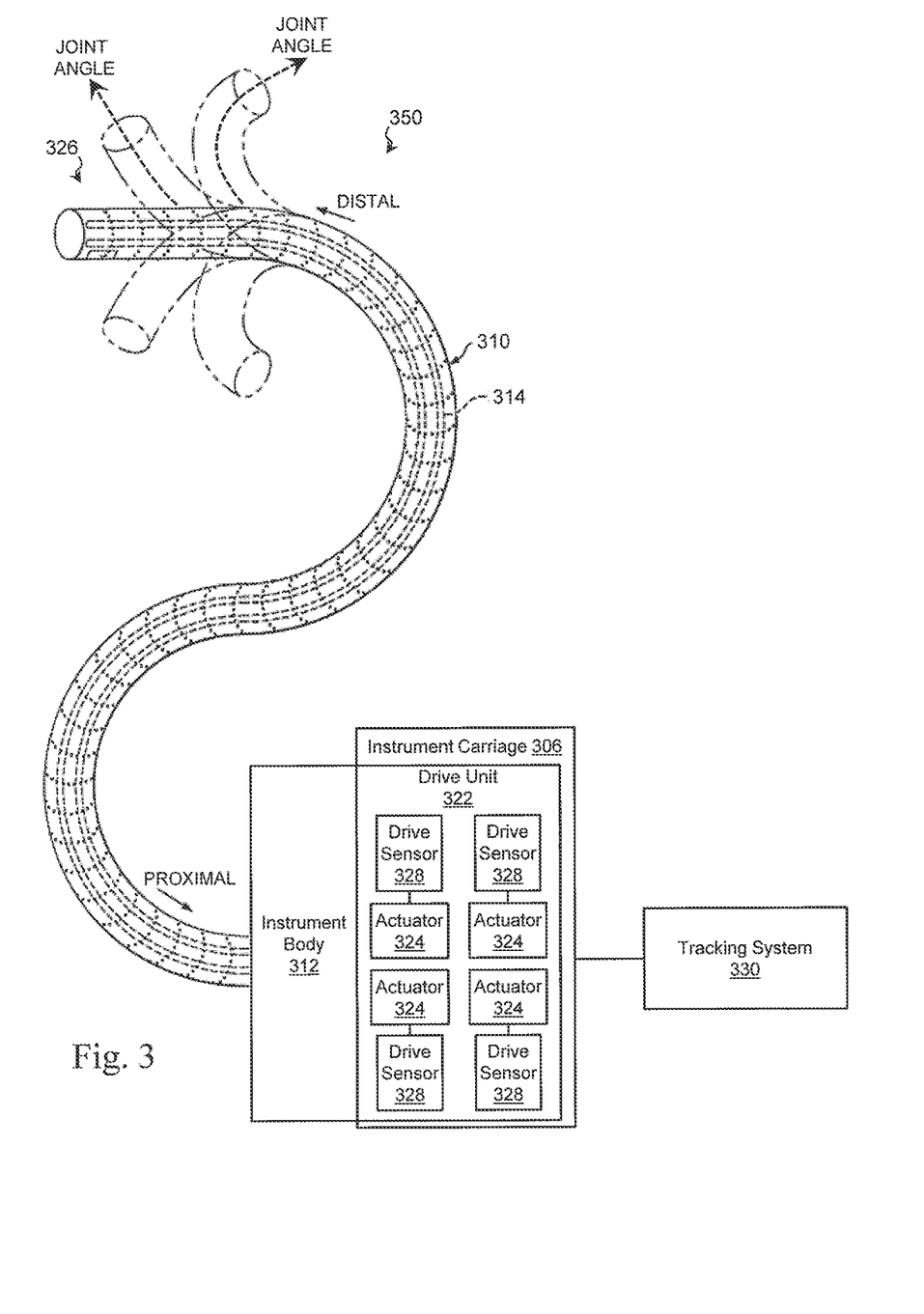
FIG. 3 is a simplified diagram of a system according to some embodiments.

FIG. 3 is a simplified diagram of a robotic system 350 according to some embodiments. The system 350 includes a flexible elongate device 310 and an instrument body 312 that releasably couples to an instrument carriage 306, each of which may be substantially similar to those described in FIGS. 2A and 2B.

The flexible elongate device 310 may have an articulatable portion (e.g., distal portion 326) that may be articulated steered) in one or more degrees of freedom to guide the elongate device 310 through branching passageways. For this purpose, the flexible elongate device 310 may include a number of articulation controls (e.g., cables, linkages, pull wires, tendons, or other articulation controls) that extend from the articulatable portion, through the flexible elongate device 310, and to chive inputs (e.g., input disks) of the instrument body 312.

The instrument carriage 306 may comprise, a drive unit 322 having drive outputs. Coupling the flexible elongate device 310 and the instrument body 312 to the instrument carriage 306 may comprise coupling drive outputs of the drive unit 322 to drive inputs of the instrument body 312. This may create a drive connection between a set of actuators 324 in the drive unit 322 and the articulatable portion of the flexible elongate device 310. The actuators may use the drive connection to cause articulatable portions (e.g., the distal portion 326) of the flexible elongate device 310 to articulate. In various embodiments, the actuators 324 may include servomotors, rotary actuators, linear actuators, and/or other actuating mechanisms that apply force to the articulation controls and thereby move the flexible elongate device 310. Suitable drive units 322 and articulation controls are described in detail in U.S. Pat. No. 7,316,681 (filed on Oct. 4, 2005 and titled "Articulated Surgical Instrument for Performing Minimally Invasive Surgery with Enhanced Dexterity and Sensitivity") and U.S. Pat. No. 9,259,274 (filed Sep. 30, 2008 and titled "Passive Preload and Capstan Drive for Surgical Instruments"), which are incorporated by reference herein in their entireties.

The drive unit 322 may include one or more drive sensors 328 coupled to the actuators 324 to measure articulation in the degrees of freedom based on actuator movement, force, and/or other properties. In some embodiments, the drive sensors 328 may include position resolvers, encoders, potentiometers, and/or other suitable sensors coupled to the actuators 324 to measure and report movement in the corresponding actuator 324. In some embodiments, the drive sensors 328 may include force, strain, and/or torque sensors coupled to measure and report an amount of force imparted by the respective actuator 324. These measurements and others may be used to determine the extent of articulation, which may be characterized as a bend radius, an angle of the articulated portion relative to an orientation of a non-articulated portion of the elongate device 310 (e.g., joint angle), or other suitable characterization.

Data from the drive sensors 328, along with data from sensors associated with the flexible elongate device 310, may be provided to a tracking system 330 of the system 350. In some embodiments, the tracking system 330 may be part of the control system 112 described above. The tracking system 330 may utilize the received data to determine the position, orientation, speed, velocity, pose, and/or shape of the distal portion 326 and/or of one or more segments along the flexible elongate device 310. For example, the tracking system 330 may determine the shape of the flexible elongate device 310 based on data from the drive sensors 328 and/or data from the articulation sensor 314 (e.g., one or more shape sensors or position sensors, such as fiber optic sensors, electromagnetic position sensors, etc.) disposed within the flexible elongate device 310. The tracking system 330 may also consider historical pose data to reconstruct the shape of the flexible elongate device 310 over an interval of time.

Tracking system 330 may optionally be implemented as hardware, firmware, software or a combination thereof which interact with or are otherwise executed by one or more computer processors, which may include the processors of control system 112 of FIG. 1. For example, the tracking system 330 may comprise one or more processors and non-transitory computer memory storing machine-executable instructions that, when executed by the one or more processors, cause the tracking system 330 to perform various operations as described herein.

The tracking system 330 and the drive unit 322 may be used to perform a set of calibration tests of the system 350, some of which are described with reference to FIGS. 4, 5A, and 5B. For example, prior to performing a procedure using the flexible elongate device 310 or other articulating elements of the system 350, to the system 350 may verify proper articulation of the flexible elongate device 310, verify feedback loops that control articulation of the flexible elongate device 310, calibrate the sensors of the system 350, and/or assess other properties of the system 350 and/or the flexible elongate device 310 that may affect the ability to reliably maneuver the flexible elongate device 310. Accordingly, in some embodiments, one or more test procedures may be performed that include articulating the elongate device 310 in one or more degrees of freedom and collecting sensor data for these test purposes and others.

Figure 4:
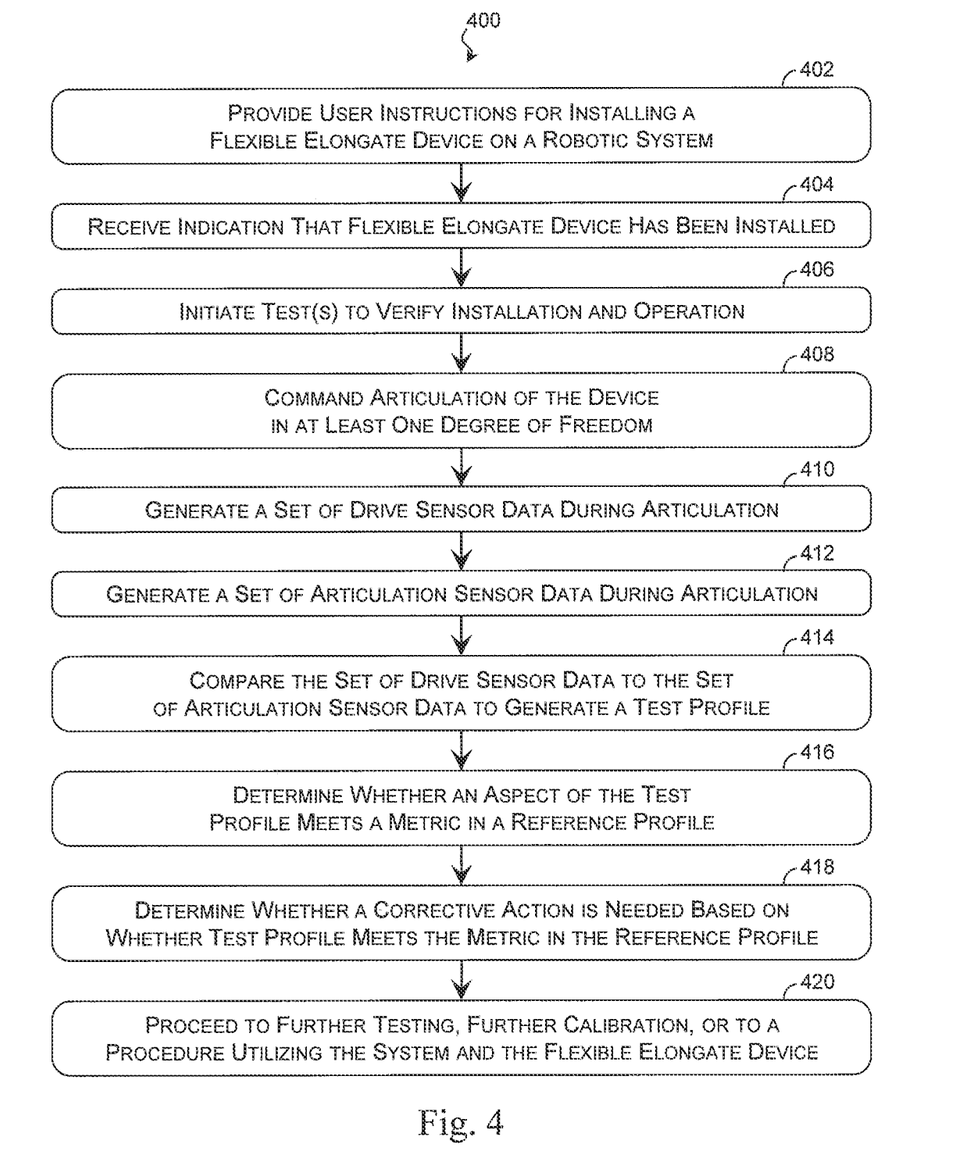
FIG. 4 is a flowchart illustrating a method of comparing drive sensor data to articulation sensor data according to some embodiments.

FIG. 4 is a flowchart describing an example method 400 of comparing drive sensor data to articulation sensor data according to some embodiments. The method 400 may be used to calibrate the system 350, for example. The method 400 is illustrated in FIG. 4 as a set of operations or processes. The processes illustrated in FIG. 4 may be performed in a different order than the order shown in FIG. 4, and one or more of the illustrated processes might not be performed in some embodiments of method 400. Additionally, one or more processes that are not expressly illustrated in FIG. 4 may be included before, after, in between, or as part of the illustrated processes. In some embodiments, one or more of the processes of method 400 may be implemented, at least in part, in the form of executable code stored on non-transitory, tangible, machine-readable media that, when run by one or more processors (e.g., the processors of the tracking system 330 and/or the control system 112), may cause the one or more processors to perform one or more of the processes. FIGS. 5A and 5B are diagrams illustrating relationships between sets of sensor data during the method 400 of testing and/or calibrating the system 350 according to some embodiments.

Referring to process 402 of FIG. 4, the robotic system 350 may provide user instructions for installing a flexible elongate device 310 on the system 350. In some examples, the flexible elongate device 310 and a coupled instrument body 312 may be supplied separately from the remainder of the system 350, and process 402 may provide instructions to an operator O for coupling the flexible elongate device 310 and the instrument body 312 to the instrument carriage 306 of the system 350. This may include connecting drive inputs of the instrument body 312—and thereby connecting articulation controls of the flexible elongate device 310—to the actuators 324 of the drive unit 322 of the instrument carriage 306. The instructions may include visual and/or auditory instructions and may be presented via a display system 110, via indicators on the instrument carriage 306, and/or other suitable mechanisms.

Referring to process 404 of FIG. 4, the tracking system 330 of the system 350 may receive an indication that the flexible elongate device 310 has been installed. For example, the indication may represent that the flexible elongate device 310 and the instrument body 312 have been coupled to the instrument carriage 306 of the system 350. Referring to process 406 of FIG. 4, after the flexible elongate device 310 has been installed, the system 350 may initiate one or more tests, such as a fitting test, to verify the installation and proper operation of the flexible elongate device 310.

Referring to process 408, the tracking system 330 may perform the fitting test by commanding articulation of the flexible elongate device 310 in at least one degree of freedom. For example, the tracking system 330 may command articulation by activating an actuator 324 associated with a degree of freedom. The actuator 324 may turn a capstan within the instrument body 312 that rotates to wind a cable of the flexible elongate device 310 around the capstan and thereby effect movement of a portion (e.g., distal portion 326) of the flexible elongate device 310.

The tracking system 330 may command articulation of the flexible elongate device 310 in any suitable pattern. For example, the tracking system 330 may first command the flexible elongate device 310 to move from a neutral position to a first point in a first direction in one or more degrees of freedom being exercised. The tracking system 330 may determine that the flexible elongate device 310 has reached the first point based on any suitable sensor data including that obtained during processes 406 and/or 408, described in more detail below. The first point may be a physical limit of the flexible elongate device 310 in the degree of freedom, or the first point may be less than the physical limit (e.g., 50% of the physical limit) of the flexible elongate device 310 to avoid overextension and/or because the sensors might not yet be fully calibrated. After the flexible elongate device 310 has reached the first, point, the tracking system 330 may command the flexible elongate device 310 to move from the first point past the neutral position to a second point in a second direction in the degree of freedom opposite the first direction. As with the first point, the second point may be any point up to a physical limit of the flexible elongate device 310 in the second direction. This may be repeated for any number of cycles.

Referring to process 410, the tracking system 330 may generate a set of drive sensor data in response to the commanded articulation of process 408. The drive sensor data may be obtained from the drive sensors 328 of the drive unit 322 and/or other sensors of the tracking system 330. The drive sensor data may include position data of the actuators 324 and/or may include force data, strain data, torque data, and/or other data representing a relationship between the actuators 324 and the flexible elongate device 310. The drive sensor data may be associated with motion in at least one degree of freedom. In some examples, the drive sensor data may be associated with motion in a single degree of freedom, and the test may be repeated in order to obtain sensor data in other degrees of freedom. In some examples, the method 400 may verify operation in more than one degree of freedom concurrently, and the drive sensor data may be associated with motion in two or more degrees of freedom.

Referring to process 412, the tracking system 330 may generate a set of articulation sensor data in response to the commanded articulation of process 408. The articulation sensor data may be obtained from sensors of the flexible elongate device 310 such as the articulation sensor 314 (e.g., fiber optic shape sensors, EM position sensors, etc.) and/or other suitable sensors. As with the drive sensor data, the articulation sensor data may be associated with motion in at least one degree of freedom. In some examples, the articulation sensor data may be associated with motion in a single degree of freedom, and the test may be repeated in order to obtain sensor data in other degrees of freedom. In some examples, the method 400 may verify operation in more than one degree of freedom concurrently, and the articulation sensor data may be associated with motion in two or more degrees of freedom.

Referring to process 414, the tracking system 330 may compare the set of drive sensor data obtained in process 410 to the set of articulation sensor data obtained in process 412 to generate a test profile. Because the drive sensor data and the articulation sensor data may represent different properties, the tracking system 330 may convert either or both to a common measurement. For example, the tracking system 330 may convert drive sensor data (e.g., actuator position data) into a measure of the extent of articulation in a given degree of freedom, which may be characterized as a distal end bend radius, an angle of an articulated portion of the elongate device 310 relative to a non-articulated portion of the elongate device 310 (e.g., the joint angle of FIG. 3), and/or other suitable measure. The tracking system 330 may also convert the articulation sensor data into a corresponding measure of the extent of articulation, such as a distal end bend radius, an angle of an articulated portion, etc.

Figure 5A:
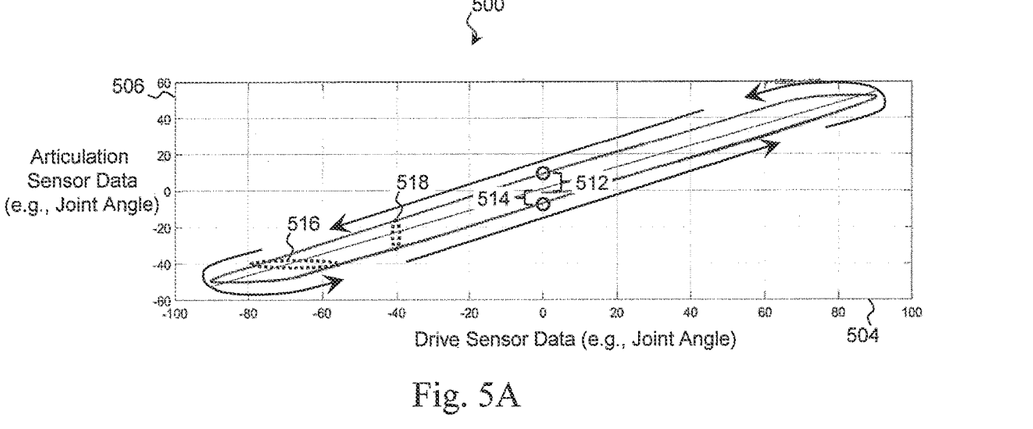
FIGS. 5A and 5B are diagrams illustrating a relationship between sets of sensor data during a method of testing and/or calibrating a system according to some embodiments.
Figure 5B:
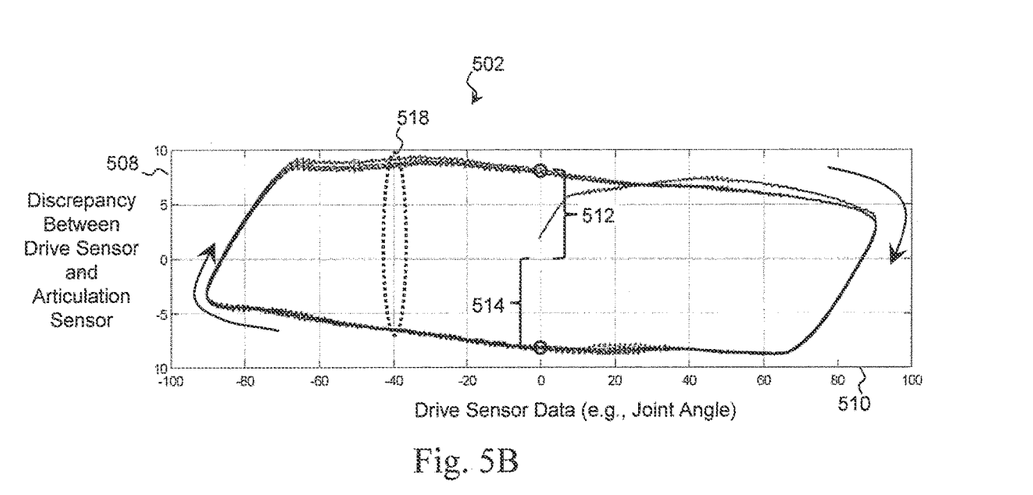

The plot 500 of FIG. 5A illustrates a comparison between an example set of drive sensor data (e.g., actuator position data) having been converted into a measure of an extent of articulation (e.g., joint angle), plotted along axis 504, and an example set of articulation sensor data having been converted into a corresponding measure of the extent of articulation (e.g., joint angle), plotted along axis 506. Due to manufacturing tolerances, installation issues, maintenance issues, calibration issues, and/or other reasons, the drive sensor data may differ from the articulation sensor data. The plot 502 of FIG. 5B shows this discrepancy in another way and illustrates an arithmetic difference or other measure of discrepancy between the drive sensor data and the articulation sensor data, plotted along axis 508, and the extent of articulation in either the drive sensor data or the articulation sensor data, plotted along axis 510.

From the test profile, it can be determined whether or not the system 350 and/or flexible elongate device 310 are within tolerances, and if not, determine what corrective action to take. To do so, referring to process 416 of FIG. 4, the tracking system 330 may determine whether one or more aspects of the test profile meets one or more metrics—such as thresholds—in a reference profile. The reference profile may include a set of predetermined thresholds for the one or more metrics and the thresholds may be determined via calibration procedures at manufacturing time, via analytical considerations based on the design of the device 310, and/or via characterization of a statistically relevant sample of elongate devices throughout their expected life. The reference profile may be stored in a memory (e.g., non-volatile memory) of the device 310 and/or a memory of the system 350.

In some examples, the aspect may include an offset of the test profile and the metric may include an offset threshold of the reference profile. Referring to markers 512 and 514 in FIGS. 5A and 5B, the tracking system 330 may measure the neutral position offset based on the amount of articulation measured by the articulation sensor data when the drive sensor data indicates no articulation or no force applied by the actuators (e.g., the neutral position). The (racking system 330 may then determine whether the articulation in the articulation sensor data is within a predetermined threshold (e.g., 0±5°, 0±10°, etc.) of the reference profile.

In some examples, the aspect may include a slope, and the metric may include a slope threshold. For example, in process 416, the tracking system 330 may determine a slope fit between the amount of articulation measured by the drive sensor data and the amount of articulation measured by the articulation sensor data. The tracking system 330 may determine whether the slope is within a predetermined threshold (e.g., 1.0±10%) of the reference profile.

In some examples, the aspect may include a maximum discrepancy, and the metric may include a suitable threshold. For example, in process 416, the tracking system 330 may determine whether a maximum discrepancy between the amount of articulation measured by the drive sensor data and the amount of articulation measured by the articulation sensor data is within a predetermined threshold (e.g., ±5°, ±10°, etc.) of the reference profile.

In some examples, the aspect may include sensor hysteresis, and the metric may include a hysteresis threshold. For example, in process 416, the tracking system 330 may determine the hysteresis in the drive sensor data and the articulation sensor data by comparing the amount of articulation measured by the drive sensor data and/or the articulation sensor data when the elongate device 310 is traveling in a first direction to the amount of articulation measured by the drive sensor data and/or the articulation sensor data when the elongate device 310 is traveling in a second direction. Hysteresis may be measured in terms of either set of data as indicated by markers 516 and 518 of FIGS. 5A and 5B. The tracking system 330 may determine whether the hysteresis is within a predetermined threshold (e.g., a delta of 5°, 10°, etc.) of the reference profile.

In some examples, the aspect may include linearity, and the metric may include a linearity threshold. For example, in process 416, the tracking system 330 may determine a measure of the linearity of the amount of articulation measured by the drive sensor data and the amount of articulation measured by the articulation sensor data. The measure may include any suitable linearity metric such as an average of the residuals, a standard deviation of the residuals, a maximum or minimum of the residuals, distribution of the residuals via a chi-squared test (e.g., Pearson's chi-squared test) and/or other suitable metric. The tracking system 330 may determine whether the measure of linearity is within a predetermined threshold of the reference profile.

In some examples, the aspect may include noise in the drive sensor data and/or the articulation sensor data, and the metric may include a noise threshold. For example, in process 416, the tracking system 330 may determine whether noise in the amount of articulation measured by the drive sensor data and/or the amount of articulation measured by the articulation sensor data is within a predetermined threshold of the reference profile. In an example, the tracking system 330 may compare a maximum absolute value of the residuals of the drive sensor data and the articulation sensor data to a threshold. In making the comparison, the maximum absolute value may be multiplied by a margin coefficient based on sampling confidence. Additionally or in the alternative, the tracking system 330 may compare standard deviation and/or variance of the residuals to a respective thresholds.

In some examples, in process 416, the flexible elongate device 310 may be installed in more than one orientation, or elements of the flexible elongate device 310 such as the articulation sensor 314 may be installed in more than one orientation during manufacturing. For example, the articulation sensor 314 may contain four bundles of optical fibers arranged so that the sensor may be installed in the elongate device 310 in one of four rotational orientations relative to the rest of the device 310 (e.g., 0°, 90°, 180°, or −90°). Accordingly, in such embodiments, the tracking system 330 determines from the test profile how the drive sensor data is oriented to the articulation sensor data and/or how the respective sensors are oriented to the degree(s) of freedom.

Referring to process 418, the tracking system 330 may determine whether a corrective action may be needed based on the comparison of process 414 and/or 416. For example, the results of process 414 and/or 416 may be used to adjust the calibration of the respective sensors, to adjust feedback loops used to articulate the flexible elongate device 310 into a particular pose, and/or to diagnose and correct a number of problems with the flexible elongate device 310 and/or the system 350. These may include installation issues, drivetrain faults such as derailment, broken cables, binding, stretching, excessive compliance or friction, and/or others. If the test profile fails to meet any of the above thresholds or other metrics in the reference profile, an operator may be instructed to service, reinstall, or replace flexible elongate device 310 and/or another component of system 350. In contrast, when the test, profile meets the metrics of the reference profile, the method 400 may proceed to further calibration or may proceed to a medical procedure using the system 350, as indicated by process 420. In some examples, further calibration may include repeating one or more of processes 406-418 for additional (e.g., untested) degrees of freedom.

Figure 6:
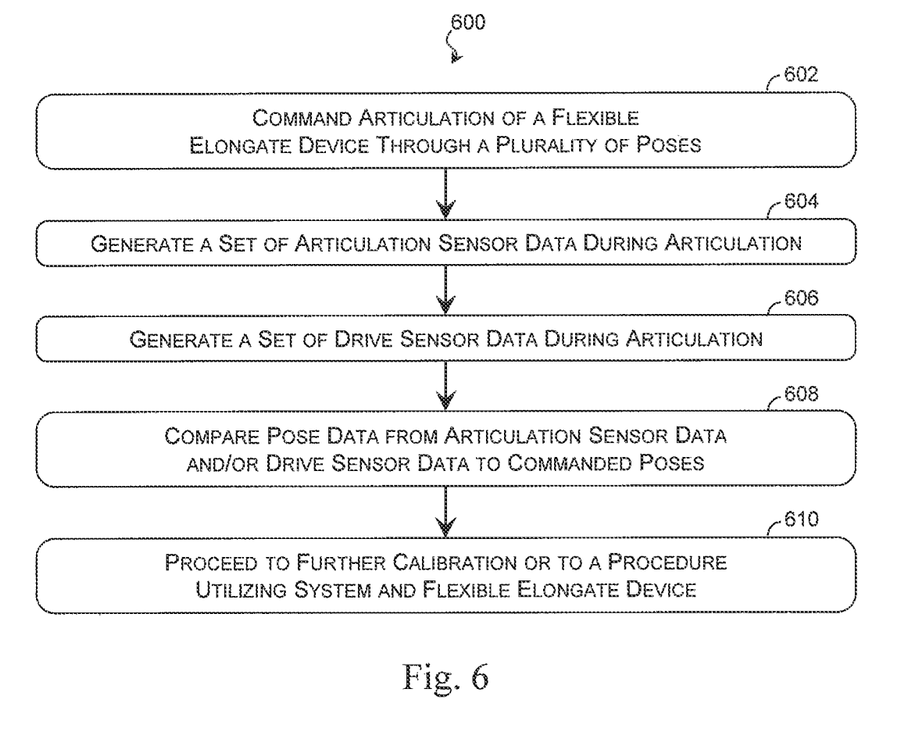
FIG. 6 is a flowchart illustrating a method of comparing pose data to commanded poses according to some embodiments.

Examples of additional calibration tests are described with reference to FIG. 6, which is a flowchart describing a method 600 of comparing pose data to commanded poses according to some embodiments. For example, the method 600 may be used for bend strain testing the system 350. The processes illustrated in FIG. 6 may be performed in a different order than the order shown in FIG. 6, and one or more of the illustrated processes might not be performed in some embodiments of method 600. Additionally, one or more processes that are not expressly illustrated in FIG. 6 may be included before, after, in between, or as part of the illustrated processes. In some embodiments, one or more of the processes of method 600 may be implemented, at least in part, in the form of executable code stored on non-transitory, tangible, machine-readable media that, when run by one or more processors (e.g., the processors of the tracking system 330 and/or the control system 112), may cause the one or more processors to perform one or more of the processes. The method 600 may be performed at any time and, in some embodiments, may be performed after the system 350 has successfully completed method 400.

Referring to process 602, the tracking system 330 of the system 350 may command articulation of the flexible elongate device 310 through a plurality of poses. The tracking system 330 may command articulation by activating the actuators 324 of the drive unit 322. For example, the tracking system 330 may activate more than one actuator 324 to achieve a particular pose in contrast to activating each actuator 324 individually. The tracking system 330 may utilize a feedback loop to activate the actuator(s) 324 until the tracking system 330 determines that the flexible elongate device 310 has achieved the pose or until another limit is met (e.g., a maximum operating tension). The tracking system 330 may determine that the flexible elongate device 310 has reached a pose based on any suitable sensor data including that obtained during processes 604 and/or 606, described in more detail below. In some examples, the system 350 may utilize drive sensor data when moving the flexible elongate device 310 in process 408 of method 400, and, after properly calibrated the articulation sensors (e.g., shape sensors) in method 400, may utilize articulation sensor data to determine when the flexible elongate device 310 has achieved a particular pose in process 602 of method 600.

The plurality of poses in process 602 may include any suitable poses. In some examples, the system 350 may move the flexible elongate device 310 to positions less than the physical limit of the flexible elongate device 310, such as in process 408 of method 400 in some scenarios. After the sensors have been properly calibrated (e.g., in method 400), the tracking system 330 may command articulation of the flexible elongate device 310 to poses at or near a physical limit (e.g., in process 602 of method 600). Because the sensors used to control articulation (e.g., articulation sensor 314) have been properly calibrated and verified, the risk of overextension of the elongate device 310 may be reduced.

As explained above, a given pose may include: movement in more than one degree of freedom. This may be leveraged to detect issues in the system 350 and/or the flexible elongate device 310 that arise when motion in more than one degree of freedom is involved. It may also be leveraged to test a full range of motion in fewer poses than testing each degree of freedom individually. For example, the tracking system 330 may command articulation of the flexible elongate device 310 from a neutral position to a first pose in a first direction in a first degree of freedom without articulation in a second degree of freedom. The first pose may be at a physical limit in the first direction. The tracking system 330 may then command articulation of the flexible elongate device 310 back to the neutral position. The tracking system 330 may then command articulation of the flexible elongate device 310 from the neutral position to a second pose in a second direction in the first degree of freedom and in a third direction in the second degree of freedom. The second pose may be at a physical limit in the second direction and/or at a physical limit in the third direction. For some flexible elongate devices 310, the physical limit in a given degree of freedom may vary depending on the amount of articulation in another degree of freedom. For example, whereas the first pose may have a joint angle of (−180°, 0), the second pose may have a joint angle of (127°, 127°). Continuing the example, the tracking system 330 may then command articulation of the flexible elongate device 310 from the second pose back to the neutral position. The tracking system 330 may command articulation of the flexible elongate device 310 from the neutral position to a third pose in the second direction in the first degree of freedom and in a fourth direction in the second degree of freedom (e.g., a pose angle of (127°, −127°)). The third pose may be at a physical limit in the second direction and/or at a physical limit in the fourth direction. In this way, the poses may achieve a comprehensive test of the full range of motion in two degrees of freedom with only three poses. Of course, other examples utilize any number of poses.

Referring to process 604, the tracking system 330 may generate a set of articulation sensor data in response to the commanded articulation of process 602. This may be performed substantially as described above, and the articulation sensor data may be obtained from sensors of the flexible elongate device 310 such as the articulation sensor 314 (e.g., fiber optic sensors, EM position sensors, and/or other suitable sensors).

Referring to process 606, the tracking system 330 may generate a set of drive sensor data in response to the commanded articulation of process 602. The drive sensor data may be obtained from the drive sensors 328 of the drive unit 322 and/or other sensors of the system 350. The drive sensor data may include position data of the actuators 324 and/or may include force data, strain data, torque data, and/or other data representing a relationship between the actuators 324 and the flexible elongate device 310.

Referring to process 608, the tracking system 330 may compare pose data from the set of articulation sensor data obtained in process 604 and/or the set of drive sensor data obtained in process 606 to the commanded pose(s). The tracking system 330 may consider any suitable aspect of the pose data, including those described above in the context of process 416. In some examples, the tracking system 330 may determine whether an offset of any measurement of the pose data at the neutral position or at any of the commanded poses exceeds a respective threshold. In some examples, the tracking system 330 may determine whether a rate of change (e.g., slope) of the pose data during the travel to a given pose is within a respective threshold. In some examples, the tracking system 330 may determine whether hysteresis of the pose data meets a respective threshold. In some examples, the tracking system 330 may determine whether a noise measurement, such as RMS noise, in the pose data meets a corresponding threshold.

In some examples, the tracking system 330 may consider the continuity of the pose data during the travel to each pose. In this regard, certain types of sensors, such as optical fiber shape sensors 314, may be prone to breakage, separation, or other discontinuity when the flexible elongate device 310 is flexed. This type of error can be detected from the pose data continuity.

Method 600 may be used to assess the calibration of the sensors of the system 350. The results of process 608 may be used to detect a number of problems with the flexible elongate device 310 and/or the system 350, including installation issues, drivetrain faults such as derailment, broken cables, binding, stretching, excessive compliance or friction, and/or others. If the test profile fails to meet certain metrics, the flexible elongate device 310 may be serviced, reinstalled, or replaced. In contrast, if process 608 indicates that system 350 and flexible elongate device 310 pass verification, the results may be used to maintain or adjust the calibration of the respective sensors and/or to maintain or adjust feedback loops used to articulate the flexible elongate device 310 into a particular pose. The method 600 may then proceed to further calibration or may proceed to a medical procedure using the system 350, as indicated by process 610.

VARIOUS EXAMPLES OF IMPLEMENTATIONS OF THE DISCLOSURE

This disclosure describes various instruments and portions of instruments in terms of their state in three-dimensional space. For example, the term position refers to the location of an object or a portion of an object in a three-dimensional space (e.g., three degrees of translational freedom along Cartesian x-, y-, and z-coordinates). The term orientation refers to the rotational placement of an object or a portion of an object (e.g., one or more degrees of rotational freedom, such as roll, pitch, and yaw). The term pose refers to the position of an object or a portion of an object in at least one degree of translational freedom and to the orientation of that object or portion of the object in at least one degree of rotational freedom (e.g., up to six total degrees of freedom). The term shape refers to a set of poses, positions, or orientations measured along an object.

One or more elements in embodiments of this disclosure may be implemented in software to execute on a processor of a computer system such as control processing system. When implemented in software, the elements of the embodiments of this disclosure may be code segments to perform various tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and/or magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. Any of a wide variety of centralized or distributed data processing architectures may be employed. Programmed instructions may be implemented as a number of separate programs or subroutines, or they may be integrated into a number of other aspects of the systems described herein. In some examples, the control system may support wireless communication protocols such as Bluetooth, Infrared Data Association (IrDA), HomeRF, IEEE 802.11, Digital Enhanced Cordless Telecommunications (DECT), ultra-wideband (UWB), ZigBee, and Wireless Telemetry.

Medical tools may be delivered through the flexible elongate devices (e.g., catheters) disclosed herein and may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. Medical tools may include image capture probes that include a stereoscopic or monoscopic camera for capturing images (including video images). Medical tools may additionally house cables, linkages, or other actuation controls that extend between its proximal and distal portions to controllably bend the distal portion of a medical tool. Steerable instruments are described in detail in U.S. Pat. No. 7,316,681 (filed on Oct. 4, 2005 and titled "Articulated Surgical Instrument for Performing Minimally Invasive Surgery with Enhanced Dexterity and Sensitivity") and U.S. patent application Ser. No. 12/286,644 (filed Sep. 30, 2008 and titled "Passive Preload and Capstan Drive for Surgical Instruments"), which are incorporated by reference herein in their entireties.

The systems described herein may be suited for navigation and treatment of anatomic tissues, via natural or surgically created passageways, in any of a variety of anatomic systems, including the lung, colon, intestines, kidneys and kidney calices, brain, heart, circulatory system including vasculature, and/or the like.

Note that the processes and displays presented might not inherently be related to any particular computer or other apparatus. Various general-purpose systems may be used with programs in accordance with the teachings herein, or it may prove convenient to construct a more specialized apparatus to perform the operations described. In addition, it will be appreciated that a variety of programming languages may be used to implement the examples described herein.

While certain examples have been described and shown in the accompanying drawings, it is to be understood that such examples are merely illustrative of and are not restrictive, and that the described examples are not limited to the specific constructions and arrangements shown and described, since various other modifications may occur to those ordinarily skilled in the art.

What is claimed is:

1. A robotic system comprising:
an instrument carriage configured to receive an elongate device, wherein the instrument carriage comprises a set of actuators configured to drive the elongate device along at least one degree of freedom and a set of drive sensors configured to monitor the set of actuators; and
a tracking system coupled to the instrument carriage and configured to:
receive an indication that the elongate device is installed on the instrument carriage;
operate the set of actuators to articulate a distal portion of the elongate device in at least one degree of freedom;
generate a set of drive sensor data from the set of drive sensors during the articulation;
generate a set of articulation sensor data from a shape sensor of the elongate device during the articulation;
compare the set of drive sensor data to the set of articulation sensor data to generate a test profile;
determine whether the test profile corresponds to a reference profile; and
determine whether a corrective action is needed for the elongate device based on whether the test profile corresponds to the reference profile.

2. The robotic system of claim 1, wherein the robotic system further comprises a display system configured to display an instruction for an operator to install the elongate device.

3. The robotic system of claim 1, wherein the tracking system is further configured to:
determine a first set of joint angles from the set of drive sensor data;
determine a second set of joint angles from the set of articulation sensor data; and
compare the set of drive sensor data to the set of articulation sensor data to generate the test profile based on a comparison of the first set of joint angles to the second set of joint angles.

4. The robotic system of claim 1, wherein the tracking system is configured to determine whether the test profile corresponds to the reference profile based on a neutral position offset of at least one of the set of drive sensor data or the set of articulation sensor data.

5. The robotic system of claim 1, wherein the tracking system is configured to determine whether the test profile corresponds to the reference profile based on a slope of at least one of the set of drive sensor data or the set of articulation sensor data.

6. The robotic system of claim 1, wherein the tracking system is configured to determine whether the test profile corresponds to the reference profile based on a discrepancy between the set of drive sensor data and the set of articulation sensor data.

7. The robotic system of claim 1, wherein the tracking system is configured to determine whether the test profile corresponds to the reference profile based on a linearity of at least one of the set of drive sensor data or the set of articulation sensor data.

8. The robotic system of claim 1, wherein the tracking system is configured to determine whether the test profile corresponds to the reference profile based on a noise measurement of at least one of the set of drive sensor data or the set of articulation sensor data.

9. The robotic system of claim 1, wherein the tracking system is configured to determine whether the test profile corresponds to the reference profile based on a hysteresis measurement of at least one of the set of drive sensor data or the set of articulation sensor data.

10. The robotic system of claim 1, wherein the tracking system is further configured to operate the set of actuators to articulate the distal portion of the elongate device in at least two degrees of freedom, and wherein the set of drive sensor data and the set of articulation sensor data are associated with movement in each of the at least two degrees of freedom.

11. A robotic system, comprising:
an instrument carriage configured to receive an elongate device, wherein the instrument carriage comprises a set of actuators configured to drive the elongate device along at least one degree of freedom and a set of drive sensors configured to monitor the set of actuators; and
a tracking system coupled to the instrument carriage and configured to:
receive an indication that the elongate device is installed on the instrument carriage;
operate the set of actuators to articulate a distal portion of the elongate device in at least one degree of freedom;
generate a set of drive sensor data from the set of drive sensors during the articulation;
generate a set of articulation sensor data from a shape sensor of the elongate device during the articulation;
compare the set of drive sensor data to the set of articulation sensor data to generate a test profile;
determine a rotational orientation of the shape sensor based on the test profile;
determine whether the test profile corresponds to a reference profile; and
determine whether a corrective action is needed for the elongate device based on whether the test profile corresponds to the reference profile.

12. The robotic system of claim 1, wherein operating the set of actuators includes operating the set of actuators to articulate the distal portion of the elongate device through a plurality of commanded poses; and
wherein the tracking system is further configured to monitor a positional discrepancy by comparing pose data from the shape sensor to the plurality of commanded poses during the articulation.

13. The robotic system of claim 12, wherein the tracking system is further configured to adjust a control feedback loop of the robotic system based on the positional discrepancy during the articulation to the plurality of commanded poses.

14. The robotic system of claim 12, wherein the plurality of commanded poses articulate the elongate device in a plurality of degrees of freedom.

15. The robotic system of claim 12, wherein the plurality of commanded poses includes:
a first pose with articulation in a first direction in a first degree of freedom without articulation in a second degree of freedom;

a second pose with articulation in a second direction in the first degree of freedom and in a third direction in the second degree of freedom; and a third pose with articulation in the second direction in the first degree of freedom and in a fourth direction in the second degree of freedom.

16. An apparatus comprising:

one or more processors; and non-transitory computer memory storing machine-executable instructions that, when executed by the one or more processors, cause the apparatus to:

receive an indication that a flexible elongate device is coupled to a drive unit;

command articulation of a distal portion of the flexible elongate device in at least one degree of freedom;

receive a set of drive sensor data during the articulation;

receive a set of articulation sensor data during the articulation;

compare the set of the drive sensor data to the set of the articulation sensor data to generate a test profile;

determine whether the test profile meets one or more thresholds in a reference profile; and determine whether to perform a corrective action based on whether the test profile meets the one or more thresholds.

17. The apparatus of claim 16, wherein the non-transitory computer memory stores machine-executable instructions that, when executed by the one or more processors, cause the apparatus to provide an instruction for an operator to install the flexible elongate device.

18. The apparatus of claim 16, wherein the non-transitory computer memory stores machine-executable instructions that, when executed by the one or more processors, cause the apparatus to determine a first set of joint angles from the set of the drive sensor data and a second set of joint angles from the set of the articulation sensor data.

19. The apparatus of claim 18, wherein the non-transitory computer memory stores machine-executable instructions that, when executed by the one or more processors, cause the apparatus to determine whether an offset of at least one of the first set of joint angles or the second set of joint angles at a pose meets a threshold of the one or more thresholds.

20. The apparatus of claim 18, wherein the non-transitory computer memory stores machine-executable instructions that, when executed by the one or more processors, cause the apparatus to determine whether a slope of at least one of the first set of joint angles or the second set of joint angles during the articulation meets a threshold of the one or more thresholds.

\* \* \* \* \*

UNITED STATES PATENT AND TRADEMARK OFFICE
CERTIFICATE OF CORRECTION

Page 1 of 1

PATENT NO. : 12,364,556 B2
APPLICATION NO. : 17/279730
DATED : July 22, 2025
INVENTOR(S) : Nicola Diolaiti, Wanxi Liu and Samuel B. Schorr It is certified that error appears in the above-identified patent and that said Letters Patent is hereby corrected as shown below:

In the Specification

Column 8, Line 17, change "chive" to -- drive --

Column 12, Line 2, change "(racking" to -- tracking --

Signed and Sealed this
Twenty-sixth Day of August, 2025

Coke Morgan Stewart
*Acting Director of the United States Patent and Trademark Office*